Figure 1:
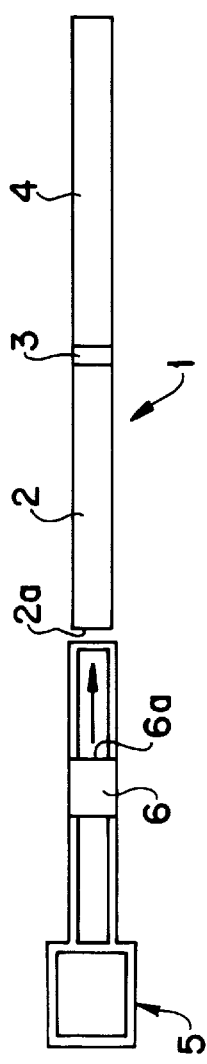

United States Patent [19]
Albertini et al.

[11] Patent Number: 6,109,093
[45] Date of Patent: Aug. 29, 2000

[54] SPLIT HOPKINSON BAR TESTING APPARATUS

[75] Inventors: Carlo Albertini, Ispra; Labibes Kamel, Angera, both of Italy

[73] Assignee: European Community, Luxembourg, Germany

[21] Appl. No.: 09/132,752

[22] Filed: Aug. 12, 1998

Related U.S. Application Data

[63] Continuation of application No. PCT/EP97/05435, Sep. 26, 1997.

[30] Foreign Application Priority Data

Dec. 12, 1996 [EP] European Pat. Off. .............. 96309085

[51] Int. Cl.⁷ ..................................................... G01M 7/00
[52] U.S. Cl. ............................................................ 73/12.08
[58] Field of Search ............................ 73/11.01, 11.03, 73/12.01, 12.05, 12.06, 12.07, 12.08

[56] References Cited

U.S. PATENT DOCUMENTS

| | | | |
|---|---|---|---|
| 3,823,786 | 7/1974 | Voitsekhovsky et al. | 173/126 |
| 3,981,379 | 9/1976 | Sayous | 181/118 |
| 4,159,039 | 6/1979 | Kasuga et al. | 173/1 |
| 4,495,792 | 1/1985 | Bai et al. | 73/12.06 |
| 5,315,364 | 5/1994 | Arion et al. | 356/32 |
| 5,487,298 | 1/1996 | Davis et al. | 73/12.05 |
| 5,549,252 | 8/1996 | Walter | 241/264 |

FOREIGN PATENT DOCUMENTS 0 410 370 A1  1/1991  European Pat. Off. ......... G01N 3/22

OTHER PUBLICATIONS

Hamdan et al, Measurement Science & Technology, vol. 7, No. 7, pp. 1068–1072 (Jul. 1996).
Staab et al, Experimental Mechanics, vol. 31, No. 3, pp. 232–235 (Sep. 1991).
Lindholm, Journal of the Mechanics and Physics of Solids, vol. 12, pp. 317–335 (1964).

*Primary Examiner*—Max Noori
*Attorney, Agent, or Firm*—Pillsbury Madison & Sutro LLP

[57] ABSTRACT

Split Hopkinson pressure bar apparatus capable of generating a compression wave or pulse in an input bar or member, said apparatus comprising an input bar or member, actuator means, a fragile or frangible component and an impactor bar or member held, in use, adjacent one end of the input bar or member and supported to resist movement in a direction away from said input bar/member when the impactor bar/member is pre-loaded in said direction by actuator means, the apparatus being such that, in use, the pre-load force can be quelled suddenly so that the impactor bar/member is released into impact or energy transfer with the input bar/member thereby transmitting a compression wave or pulse through the input bar to a specimen under test.

14 Claims, 1 Drawing Sheet

SPLIT HOPKINSON BAR TESTING APPARATUS

This is a Continuation of International Appln. No. PCT/EP97/05435 filed Sep. 26, 1997 which designated the U.S.

This invention relates to improvements in or relating to specimen testing apparatus such as that known as Hopkinson bar testing apparatus.

The use of a pressure bar such as a Hopkinson bar is well known to obtain information regarding, for example, the dynamic mechanical properties of a specimen of material placed in compression. In particular, a split Hopkinson pressure bar (SHPB) has been utilised for different case studies on the dynamic mechanical behaviour of materials. Where a study of a specimen of the material in compression is required, using a split Hopkinson pressure bar, conventionally, a compression wave is generated in the input bar by means of a cylindrical projectile fired from a gas gun to impact one end of the input bar, the other end of the input bar being connected by the specimen under test to the output bar from which information can be gathered by sensors in a well known way. However, it is believed that, at least in some circumstances, the generation of a compression wave, by firing a projectile onto the input end of the impact bar, tends to be disadvantageous more particularly in avoiding imperfect energy transfer at the interface of the forward end of the projectile coming into contact with the input end of the input bar. Theoretically, the projectile and bar should be perfectly parallel at the moment of impact with particular attention being given to guidance of the projectile inside the delivery gas gun. Additionally, the contact surfaces of the projectile and input bar at the interface need to be mechanically treated in order to preserve substantial contact between the entire front surface of the projectile and the input surface of the input bar at the moment of impact. Thus, in practice, in order to avoid energy transfer problems that can occur at the interface between the projectile and the input bar, a certain criticality of construction is required that does not allow much room for tolerance. Additionally, where a specimen of material is of increased diameter or size there will be a need to increase the diameter of the projectile with consequent modifications being needed to the gas gun to deliver such a projectile or replacement of the gun by a larger one.

It is an object of the present invention to provide apparatus for generating a compression wave or pulse in an input bar or member of a Hopkinson or pressure bar system, which apparatus at least alleviates one or more of the aforementioned, or other, problems associated with compression wave generation apparatus.

According to the present invention there is provided compression wave or pulse generation apparatus capable of generating a compression wave or pulse in an input bar or member of a pressure bar system such as a split Hopkinson pressure bar, said compression wave generation apparatus comprising an impactor bar or member held, in use, adjacent one end of the input bar or member and supported to resist movement in a direction away from said input bar/member when the impactor bar/member is pre-loaded in said direction by actuator means, the arrangement being such that, in use, the pre-load force can be quelled suddenly e.g. by rupture of a fragile or frangible component in the impactor bar/member, so that the impactor bar/member is released into impact or energy transfer with the input bar/member thereby transmitting a compression wave or pulse through the input bar to a specimen under test.

The actuator means may be any convenient means such as a hydraulic or pneumatic actuator.

Where a fragile or frangible component is provided in an impactor bar/member as aforementioned, said member is, preferably, arranged to rupture at a particular pre-set value of the preload force provided by the actuator means.

In one embodiment of the present invention, the impactor bar/member is guided and held adjacent an input end of the input bar/member (and remains adjacent the input bar during application of the preload force), preferably by means of a collar connected to one end of said impactor bar/member. In use, the collar receives the input end of the input bar and holds same adjacent the impact end of the impactor bar/member; said collar may be welded to the end of the impactor bar/member and/or may be cylindrical. Preferably, the internal diameter or dimension of the collar closely matches the external diameter or dimension of the input bar which in turn matches the diameter or dimension of the impactor bar. A blocking system or fixed support may be provided at the rear of the collar surrounding the impactor bar/member thereby resisting or preventing movement of the impactor bar in said direction on the application of the preload force. Thus, no preload force is exerted on the input bar in said direction when said preload force is applied to the inpactor bar/member.

Usually, the input bar will be connected to an output bar via the specimen to be placed under a compression test.

Further according to the present invention there is provided a method of inducing or generating a compression wave or pulse in an input bar or member of a pressure bar system such as split Hopkinson pressure bar, said method comprising pre-loading an impactor bar or member in a direction away from said input bar and suddenly removing the preload force (for example by rupturing a fragile or frangible component of the impactor bar/member) thereby releasing the impactor bar/member into impact or energy transfer with the impactor bar/member thus transmitting a compression wave through the input bar to a specimen under test.

Further advantageous apparatus and method features of the present invention will be apparent from the following description and drawings.

Figure 2:
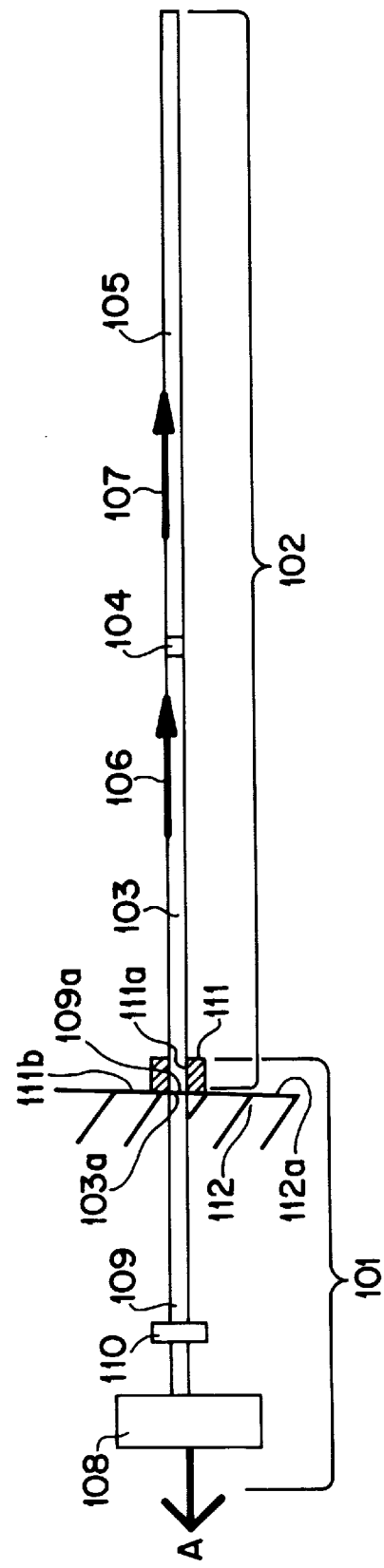

An embodiment of compression wave generation apparatus for generating a compression wave in a split Hopkinson bar will now be described, by way of example only, with reference to the accompanying very much simplified diagrammatic drawings in which:

FIG. 1 shows a longitudinal view of prior art compression wave generation apparatus and split Hopkinson pressure bar, and FIG. 2 shows a compression wave generation apparatus and a split Hopkinson pressure bar in accordance with the present invention.

FIG. 1 of the drawings shows schematically a known arrangement for generating a compression wave in a split Hopkinson pressure bar 1, comprising an input bar or member 2 connected via a specimen under test 3 to an output bar or member 4. A gas gun 5 is arranged to fire a suitable projectile 6 into impact with the free end 2a of the input bar 2 in a manner which should be self-evident from FIG. 1. Thus, the projectile generates a compression wave in the input bar 2 and hence to the specimen 3 when the front end 6a of the projectile interfaces with the end 2a of the input bar. In the example shown, the input and output bars 2,4 are a cylindrical section of similar section to that of the projectile 6.

As previously mentioned in this specification there is an interface problem in the described arrangement between the forward surface 6a of the projectile and impacted surface 2a of the input bar which can give rise to significant difficulties. In order to minimise interface problems the projectile and bar should be perfectly parallel at impact and the guidance surfaces inside the gun need to be smooth and the surfaces 6a and 2a need to be smooth and mechanically treated so that substantially the whole of the surface 6a will contact the whole of the surface 2a at impact.

FIG. 2 shows, in accordance with the present invention, compression wave generation apparatus 101 to the left of a split Hopkinson pressure bar 102. The split Hopkinson pressure bar comprises an input bar 103 connected via specimen 104, (to be tested in compression) to an output bar 105. The large arrows 106 and 107 represent the direction of a compression wave generated throughout the Hopkinson bar 102. The compression wave generation apparatus 101 has a hydraulic actuator 108 (the form of actuator could be any convenient means for example pneumatic rather than hydraulic operation) that in use induces a preload (represented by arrow A) force on an impactor bar or member 109, the right-hand end 109a of which is positioned adjacent the input or impact end 103a of the input bar 103. A fragile or frangible component 110 is provided along the length of the impactor bar 109, said frangible member being arranged to rupture at a particular value of the preload force provided by the actuator. The forward end 109a of the impactor 109 is guided and held adjacent the end 103a of the input bar 103 by means of a cylindrical collar 111 welded to said end 109a of the impactor 109. The internal diameter 111a of the collar 111 closely matches the diameter of the input bar 103 which in turn matches the diameter of the impactor bar 109 in a manner which should be evident from the drawings.

A blocking system or fixed support 112 is provided at the rear of the collar 111 surrounding the impactor bar 109 thereby resisting or preventing movement of the impactor bar 109 to the left of the support 112 on application of the preload force in the direction of arrow "A" by the hydraulic actuator 108. Under a preload force the rear face 111b of the collar 111 is urged tightly against the front face 112a of the blocking system 112 in such a manner that no preload force will be exerted on the input bar 103 in the direction of arrow "A". However, once the preload force reaches a known preset level, the fragile member 110 will rupture and the action force in the impactor bar will cause an impact at the interface between the impact surface 109a of the impactor bar and the input end 103a of the input bar 103 in a manner which should be self-evident. Furthermore, the impact will result in a compressive stress wave of precisely known amplitude and duration to be generated through the input bar 103, the specimen 104 and the output bar 107. Thus, the compression wave generation apparatus relies on the principle of storing elastic potential energy in the preloaded static impactor bar and then suddenly releasing that energy (for example by rupturing of a fragile member in the impactor bar) so that the impactor bar impacts the input bar. Thus, the afore-described invention in relation to FIG. 2 of the drawings avoids problems with the prior art arrangement discussed in relation to FIG. 1 owing to the unique continuous bar system 109,103 being divided into an impactor and an impacted system by the welded cylinder blocking system. The contact achieved by the impactor bar 109 and the input or impacted bar is nearly perfect and effectively the pulse generation propagates through the entire system without any noticeable pertubations unlike the arrangement described in relation to FIG. 1.

In the arrangement as described in relation to FIG. 1, if the diameter of the input bar is increased in order to test a larger specimen, the diameter of the projectile 6 necessarily needs to be increased so that the gun 5 will need modification or replacement by a gun able to deliver a larger projectile. However, in the arrangement as shown in the present invention in relation to FIG. 2, a larger diameter specimen can be tested much more easily simply by increasing the diameter of the input and output bars and impactor bar accordingly. The same actuator means 108 can be used.

Furthermore, it is also possible to change relatively easily the geometry of the Hopkinson bar to give, for example, a rectangular or square section of bar where required. In such a circumstance complex modifications would have to be made to a gas gun to send an appropriately sized projectile of similar section into impact with such a bar.

The apparatus in accordance with the present invention could be used for dynamic mechanical characterisation of concrete where three types of test specimen are generally used namely tubes, cylinders and prisms. Cylinders are used as the standard specimen in the United States, Canada and New Zealand whereas cube shapes are generally used in European countries.

It is to be noted that, in the arrangement shown in FIG. 2, the length of the preloaded bar 109 can be increased up to several meters, in order to increase the length of the compression pulse without problems of vibration or guidance as will be the case with the arrangement shown in FIG. 1 with a projectile inside a gun. Therefore, the arrangement shown in FIG. 2 has an additional advantage over the arrangement shown in FIG. 1 in that the length of the compression pulse can be increased up to several meters without such vibrational problems.

It is to be understood that the scope of the present invention is not to be unduly limited by a particular choice of terminology and that a specific term may be replaced by any equivalent or generic term. Further, it is to be understood that individual features, method or functions relating to the compression wave or pulse generation apparatus might be individually patentably inventive. The singular may include the plural and vice versa. Additionally, any range mentioned herein for any variable or parameter shall be taken to include a disclosure of any derivable subrange within that range or any particular value of the variable or parameter arranged within, or at an end of, the range or subrange.

Further according to the present invention there is provided a method of generating a compression wave in a pressure bar system such as a split Hopkinson pressure bar by utilising the elastic stored energy in a pre-loaded impactor bar/member by suddenly releasing that stored energy so that the impactor bar/member impacts an input bar.

Further according to the present invention there is provided apparatus for carrying out the above method.

The compression wave or pulse generation apparatus might be capable or adapted to generate a compression wave or pulse in a particular item or equipment (under test) rather than in a pressure bar system and such an arrangement may be patentably inventive.

What is claimed is:

1. Split Hopkinson pressure bar apparatus capable of generating a compression wave or pulse in an input bar or member, said apparatus comprising an input bar or member, actuator means, a fragile or frangible component and an impactor bar or member held, in use, adjacent one end of the input bar or member and supported to resist movement in a direction away from said input bar/member when the impactor bar/member is pre-loaded in said direction by actuator means, the apparatus being such that, in use, the pre-load force is quelled suddenly so that the impactor bar/member is released into impact or energy transfer with the input bar/member thereby transmitting a compression wave or pulse through the input bar to a specimen under test.

2. Apparatus as claimed in claim 1 in which the actuator means is hydraulic or pneumatic actuator.

3. Apparatus as claimed in claim 1 or claim 2 in which a fragile or frangible component is provided in the impactor bar.

4. Apparatus as claimed in claim 3 in which the fragile or frangible component is arranged to rupture at a particular pre-set value of the preload force provided by the actuator means.

5. Apparatus as claimed in any one of the preceding claims in which the impactor bar/member is guided and held adjacent an input end of the input bar/member.

6. Apparatus as claimed in claim 5 in which a collar is connected to one end of said impactor bar/member.

7. Apparatus as claimed in claim 6 in which the collar receives the input end of the input bar and holds same adjacent the impact end of the impactor bar/member.

8. Apparatus as claimed in claim 7 in which said collar is welded to the end of the impactor bar/member.

9. Apparatus as claimed in any one of claims 6 to 8 in which a blocking system or fixed support is provided at the rear of the collar surrounding the impactor bar/member thereby resisting or preventing movement of the impactor bar in said direction on the application of the preload force.

10. Apparatus as claimed in any one of the preceding claims in which the input bar is connected to an output bar via the specimen to be placed under a compression test.

11. A method of inducing or generating a compression wave or pulse in an input bar or member of a split Hopkinson pressure bar system, said method comprising pre-loading an impactor bar or member in a direction away from said input bar and suddenly removing the preload force by rupturing a fragile or frangible component of the impactor bar/member thereby releasing the impactor bar/member into impact or energy transfer with the impactor bar/member, thus transmitting a compression wave through the input bar to a specimen under test.

12. Apparatus as claimed in claim 1 in which the pre-load force is quelled suddenly by rupture of a fragile or frangible component in the impactor bar/member.

13. Apparatus as claimed in claim 7 in which said collar is cylindrical.

14. Apparatus as claimed in claim 7 in which the internal diameter or dimension of the collar closely matches the external diameter or dimension of the input bar which in turn matches the diameter or dimension of the impactor bar.

* * * * *